United States Patent
Klaffert (10) Patent No.: US 8,960,015 B2
(45) Date of Patent: Feb. 24, 2015

(54) LOAD TEST STAND

(71) Applicant: MBDA Deutschland GmbH, Schrobenhausen (DE)

(72) Inventor: Thomas Klaffert, Freising (DE)

(73) Assignee: MBDA Deutschland GmbH, Schrobenhausen (DE)

( * ) Notice: Subject to any disclaimer, the term of this patent is extended or adjusted under 35 U.S.C. 154(b) by 0 days.

(21) Appl. No.: 14/178,518

(22) Filed: Feb. 12, 2014

(65) Prior Publication Data

US 2014/0224035 A1    Aug. 14, 2014

(30) Foreign Application Priority Data

Feb. 13, 2013   (EP) .................... 13000733

(51) Int. Cl.
*G01N 3/02* (2006.01)
*G01M 13/02* (2006.01)

(52) U.S. Cl.
CPC ............ *G01N 3/02* (2013.01); *G01M 13/027* (2013.01)
USPC .......................................... 73/856

(58) Field of Classification Search
USPC .......................................... 73/856
See application file for complete search history.

(56) References Cited

U.S. PATENT DOCUMENTS 1,574,491 A    2/1926  Leake
4,171,803 A *  10/1979 Smith ............................ 482/83

FOREIGN PATENT DOCUMENTS

DE          38 40 261 A1     5/1990
DE       10 2006 029 556 A1  12/2007
JP           60-133350 A     7/1985

* cited by examiner

*Primary Examiner* — Lisa Caputo
*Assistant Examiner* — Jamel Williams
(74) *Attorney, Agent, or Firm* — Crowell & Moring LLP

(57) ABSTRACT

A load test stand includes a frame, a flange, and a spring mechanism. The spring mechanism is mounted on the frame and includes a symmetrical arrangement of at least four spring elements. The spring mechanism also includes frame points connecting the spring mechanism and the frame and articulation points connecting the spring mechanism and the flange. The flange can be coupled, by an adapter, to the output shaft of a servo system that is to be tested.

10 Claims, 6 Drawing Sheets

Fig. 1

Prior Art

LOAD TEST STAND

CROSS-REFERENCE TO RELATED APPLICATIONS

The present application claims priority under 35 U.S.C. §119 to European Patent Application Number 13000733.9-1557, filed Feb. 13, 2013, the entire disclosure of which is herein expressly incorporated by reference.

BACKGROUND AND SUMMARY OF THE INVENTION

The present invention relates to a load test stand, preferably for simulating load cycles. Particularly in the case of one axis servo systems or multi-axis servo systems, used in missiles or more specifically missile systems, a proof of the performance obtained while adhering to the specified data is required. In the case of rudder systems or wing servo systems for missiles it is necessary to determine, among other things, the actual values for the servo angle and/or the servo speed and/or the servo acceleration in both directions of motion as well as the bandwidth that is obtained for the specified load torques and inertias on the output side under all required environmental conditions. In addition, the simultaneous application of lateral forces on the output shafts of the servo system may also be required.

In order to simulate realistic load cycles for servo systems integrated into missile systems, active servo motor-driven or servo hydraulic-powered load test stands have already been developed. These load test stands can apply, as a function of the calculated requirements or closed simulation loops, realistic external load cycles on the output shafts of a servo system that is to be tested. Due to their very high overall cost and the limited adaptability of the load dynamics that can be obtained with different sizes of servo systems, these load test stands are available only on a limited scale.

Figure 1:
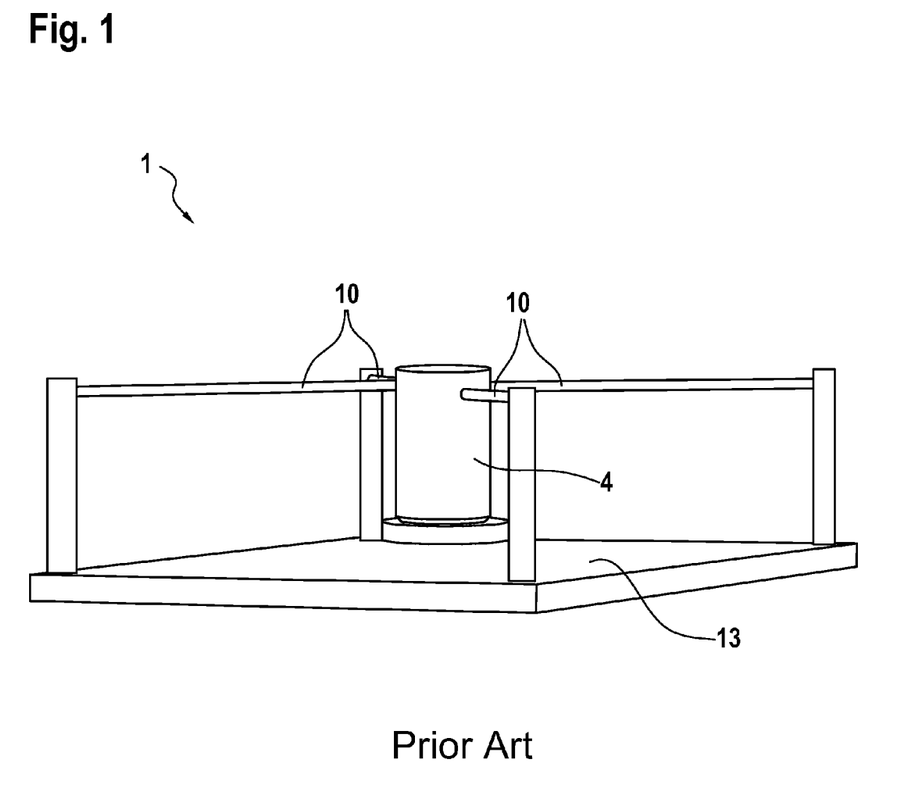

Therefore, preferably simple and economical passive load test stands are used for the sole proof of the specified servo system characteristics. The structural design of these load test stands, including interfaces, can be coordinated specifically with the requirements and special features of a specific type of servo system. In this case the applications known from the prior art are based on the following principle (see FIG. 1):

A torsion bar 10 or also a combination of several interconnected torsion bars 10 are flanged to each output shaft 6 of the servo system 4 that is to be tested. In this case the torsion bar 10 injects a torque in proportion to the change in the servo angle. Inherent deviations from the linearity can be detected by means of accurate measurements of the load test stand 1. At the same time the calibration effort with respect to such measurements is very low compared to that of active load test stands. In addition, when the torsion bars 10 are clamped in a force fitted way, the conditions for zero backlash and the necessary robustness with respect to environment factors are met in compliance with the test specification.

In principle, the net weight, which is significantly less than that of active test stands, offers better conditions for combining with other test equipment, like shakers, climate chambers, etc., but which can be used to date only conditionally for other structural and mechanical reasons, which will be described below. However, the use of almost linear torsion springs assumes that, on the one hand, the spring constant, which is to be implemented by means of the design, meets the requirements of the test specification for the servo systems, and, on the other hand, that their dimensioning permits sufficiently large servo angle ranges to be covered in compliance with all of the proofs required. This last requirement is the decisive factor that defines the minimum length of the torsion bars and, as a result, the size of the entire load test stand, which in the case of multi-axis servo systems would necessitate, in particular, very large climate chambers and with respect to its suitability for vibration tests would lead to considerable structural and mechanical problems.

In theory a scaling down of the requisite servo range and, thus, the spring size could be obtained by means of different offset angles when the torsion springs are flanged to the output shaft. In this case the necessary reclamping connected with the corresponding repetition of the required temperature cycles in the climate chambers would incur an unjustifiable expense.

Therefore, some disadvantageous consequences of known, prior art test stands include the need for enormously large and powerful climate chambers as compared to the size of the servo system to be tested as well as the resulting disadvantageous structural dimensions with respect to the three axis clampability for testing under vibration load. Therefore, in the past the latter required separate test equipment, with which only one separate function can be tested without applying torsional torques. An additional application of lateral forces on the output shafts of the servo system requires connecting one or more additional devices to the test stand configuration. In this case said additional devices are not shown in FIG. 1.

Exemplary embodiments of the present invention are directed to a load test stand, which has compact dimensions while at the same time is easy and cost-effective to produce, and which makes it possible to test servo systems in a fast and reliable way.

Specifically, exemplary embodiments of the present invention are directed to a load test stand, which exhibits a passive design. The load test stand, according to the invention, comprises a frame, a flange and a spring mechanism. The spring mechanism is mounted on the frame and comprises a, preferably symmetrical, arrangement of at least four spring elements. The flange is mounted preferably by the spring mechanism. For this purpose the spring mechanism comprises frame points connecting the frame to the spring mechanism, and comprises articulation points connecting the flange to the spring mechanism. According to the invention, the flange can be coupled, by means of an adapter, to the output shaft of a servo system that is to be tested. The use of the spring mechanism, according to the invention, allows the flange to be positionable vertically and horizontally and with respect to its neutral angle position. This arrangement enables an alignment with the output shaft of the servo system in a particularly advantageous manner. Similarly the axially elastic suspension of the flange by means of the spring mechanism makes it possible to prevent preferably undefined axial forces from being introduced into the output shaft, which could be the case, for example, in the event of temperature fluctuations. Therefore, the spring mechanism acts advantageously as a compensation element. However, the use of the spring mechanism makes it possible to apply defined lateral forces to the output shaft of the servo system to be tested in a particularly advantageous manner. Therefore, the load test stand, according to the invention, can be used preferably in a very flexible way in order to test different load conditions.

In a preferred embodiment of the invention the frame points are mounted in at least one substructure. In this way the substructure and the spring mechanism form an adjustable and/or calibratable independent module. The module can be attached, preferably by means of a universal interface, to the frame. The use of the module makes it possible to create a rigid test stand, because the module can be arranged close to the servo system to be tested. As a result, the spring mechanism is situated advantageously very close to the servo system. Thus, this arrangement enables preferably the spring mechanism to be connected rigidly with zero backlash to the servo system.

It is advantageous that a prestress of the spring mechanism and/or a position of the flange along a first axis can be adjusted by means of equidirectional changes in the position of at least two frame points of the same substructure. Therefore, in a preferred embodiment the load test stand according to the invention allows the possibility of adjusting the flange to the output shaft of the servo system along a first axis.

Furthermore, it is preferably provided that a position of the flange along a second axis can be adjusted by means of a change in the opposite direction of the position of at least two opposite frame points of different substructures. At the same time the second axis is aligned preferably perpendicularly to the aforementioned first axis. Therefore, the load test stand can enable an independent alignment of the flange along two axes that are perpendicular to each other in a particularly advantageous manner.

Finally it is preferably provided that a position of the flange along a third axis can be adjusted by means of an equidirectional change in the position of at least two opposite frame points. In this context the third axis is advantageously perpendicular to the above described two axes, so that it is possible to align the flange independently along three axes.

In order to change the position of the frame points and/or the bearing points, it is preferably provided that there are actuators. The position of the frame points and/or the bearing points can be changed in an advantageous way with these actuators. Therefore, a specified load can be applied on the flange and, thus, on the servo system by means of the test stand, so that the load test stand can be used in a very flexible way. As an alternative or in addition, it is preferably provided that the frame points and/or the bearing points can also be adjusted by hand.

Furthermore, it is preferably provided that a lateral force can be applied to an output shaft, which is part of the servo system and can be connected to the flange, by changing the position of at least one frame point. Such an arrangement also allows the load test stand, according to the invention, to test the servo system for the purpose of determining how the servo system responds to lateral forces acting on the output axes. Therefore, the load test stand enables in an advantageous way a very comprehensive testing of the servo system.

In an additional preferred embodiment a spring characteristic of the spring elements can be adjusted by means of a change in the position of the articulation points and/or the frame points. In particular, the spring characteristic of the spring elements can be adjusted by changing the relative position of the frame points to the articulation points of the spring elements. Preferably the spring characteristic can be adjusted in such a way that it exhibits linear ranges. As an alternative or in addition, the spring characteristic can be adjusted in such a way that it has at least linearizable sections. It is advantageous that the spring characteristic comprises a plurality of linear and/or linearizable sections. The advantageous use of linear and/or linearizable sections of the spring characteristic allows very simple test procedures to be carried out, because the spring force and the torsional angle are in proportion to each other.

It is advantageous that the load test stand comprises a measuring system at the flange. In particular, the measuring system is designed as an angle measuring system. Such an arrangement makes it possible to measure accurately and easily the response of the servo system. Therefore, the load test stand allows a fast and easy testing of the servo system.

Preferably the measuring system in the calibrated state forms the reference for the spring characteristic of the spring elements of the spring mechanism.

Finally it is preferably provided that at least one inertial body can be coupled to the measuring system. It is particularly preferred that the inertial body be mountable in a floating manner. Therefore, the load test stand exhibits preferably inertial bodies, wherein said inertial bodies can be, in particular, simulations of rudder units or wing units, which normally would be movable with the servo system to be tested.

Furthermore, it is preferably provided that the flange, which is elastically suspended by means of the spring mechanism in the axial direction, makes it possible to compensate for tolerances axially to the output shafts of the servo system. In particular, the spring mechanism is used to compensate for the temperature-dependent changes in tolerances. In addition, it is preferably provided that other components can also be disposed on the frame, in addition to the modules. In particular, the additional components and/or the modules can be arranged at arbitrary positions around the servo system. Furthermore, it is advantageously provided that the module, in particular the substructure of the module, comprises a protective casing, a transverse guide of the spring elements, the integration of end stops and/or safety devices when coupling to and uncoupling from the output shaft of the servo system. Finally it is preferably provided that the substructure of each module can be integrated in the frame of the load test stand. The net result of this approach is an advantageous dynamic rigidity, so that multi-axis vibration tests can also be run with the load test stand.

BRIEF DESCRIPTION OF THE DRAWING FIGURES

At this point the invention is described in detail by means of one exemplary embodiment with reference to the accompanying drawings. The drawings show in FIG. 1 a schematic view of a load test stand according to the state of the art.

DETAILED DESCRIPTION

FIG. 1 shows a test stand 1 according to the state of the art. This prior art test stand has already been described in the introductory part of the specification. The use of torsional bars 10 makes it necessary for the size of the frame 13 to be large. Therefore, the dimensions of the test stand 1 are considerably larger than the dimensions of the servo system 4 to be tested.

Figure 2:
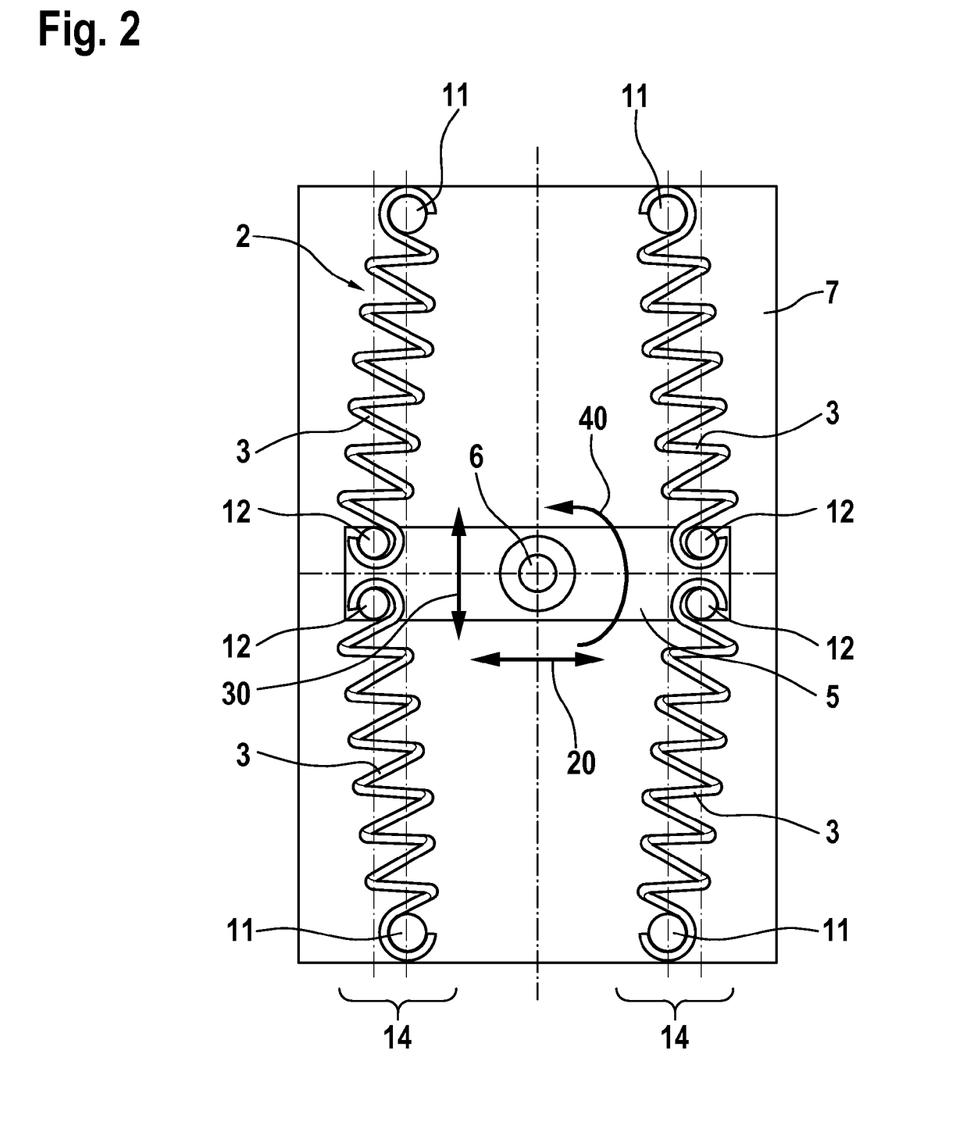
FIG. 2 a schematic view of the operating principle of the load test stand according to one exemplary embodiment of the invention.
Figure 3:
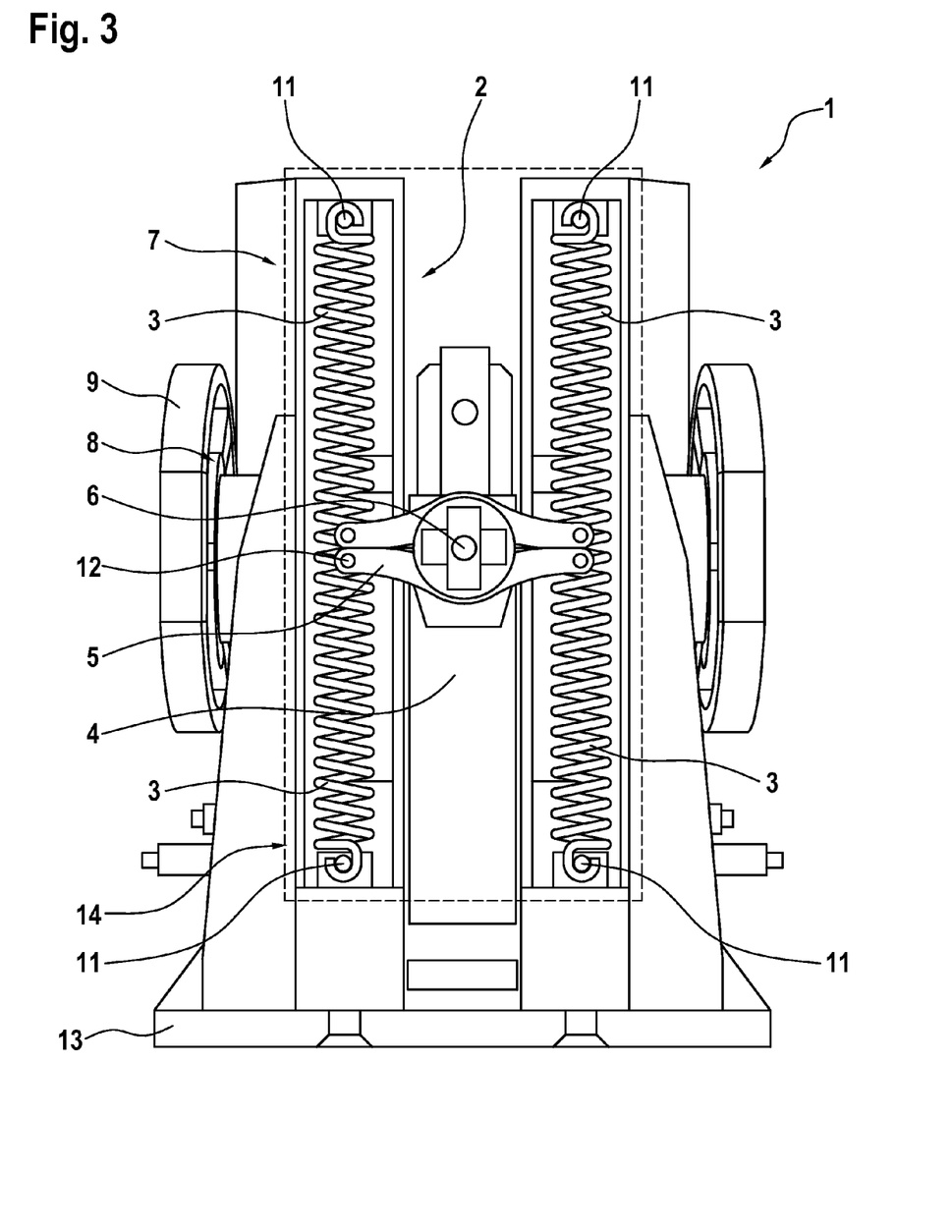
FIG. 3 a first schematic view of the load test stand according to the exemplary embodiment of the invention.

FIG. 2 shows in schematic form the operating principle of the test stand 1 according to one exemplary embodiment of the invention, whereas FIG. 3 is a schematic view of an implementation of the principle depicted in FIG. 2. For this purpose there are a plurality of spring elements 3, which form collectively a spring mechanism 2. The spring mechanism 2 forms a suspension for a flange 5, to which an output shaft 6 of a servo system 4, which is to be tested, can be connected.

Each spring element 3 is connected to the flange 5 at an articulation point 12 and is connected to the frame 13 of the test stand 1 by means of a frame point 11. The frame points 11 are mounted in a plurality of substructures 14, so that the net result is a plurality of independent modules 7.

An alignment of the flange 5 is possible by changing the position of the frame points 11 and/or the articulation points 12. In this way it is also possible to apply lateral forces to an output shaft 6, which is connected to the flange 5, in that following alignment and connection with the output shaft 6, the flange 5 is moved once more into its position. In this case the output shaft 6 serves as the abutment, so that the output shaft 6 has to absorb a lateral force.

In particular, the flange 5 can be aligned along a first axis 20, a second axis 30 and a fourth axis 40. In the drawing shown in FIG. 2, the first axis 20 and the second axis 30 are parallel to the drawing plane and are perpendicular to each other. The third axis 40 is an axis of rotation and is perpendicular to the first axis 20 and the second axis 30, so that it is possible to rotate the flange 5 inside the drawing plane.

It is possible to align the flange 5 along the first axis 20 by moving two frame points 11 of the same substructure 14 in the same direction. For example, the two frame points 11 of a substructure 14 can be moved outwards, i.e. away from the drive axis 6, in order to move by this technique the flange 5 in the same direction as the frame points 11. In the event that the frame points 11 of the same substructure were to be moved in the opposite direction, for example, one frame point 11 inwards and another frame point 11 outwards, then the position of the flange 5 would not change. However, the prestress of the spring mechanisms 2 can be enlarged in this way, because the respective spring excursion between the frame point 11 and the articulation point 12 is elongated.

If two opposite frame points 11 of different substructures 14 are moved in opposite directions, then it is possible to move the flange 5 along the second axis 30. For example, two frame points 11 can be moved away from each other, in order to move the flange 5 along the second axis 30 in the direction of the frame points 11.

Finally it is possible to rotate the flange 5 about the third axis 40 by means of an equidirectional change in the position of two opposite frame points 11 of different substructures 14.

Therefore, a position of the flange 5 can be adjusted very precisely, while at the same time all relevant directions can be adjusted independently of each other. Therefore, the inventive load test stand 1, according to the exemplary embodiment, can be adjusted very flexibly and can, therefore, be used for a plethora of applications.

Figure 4:
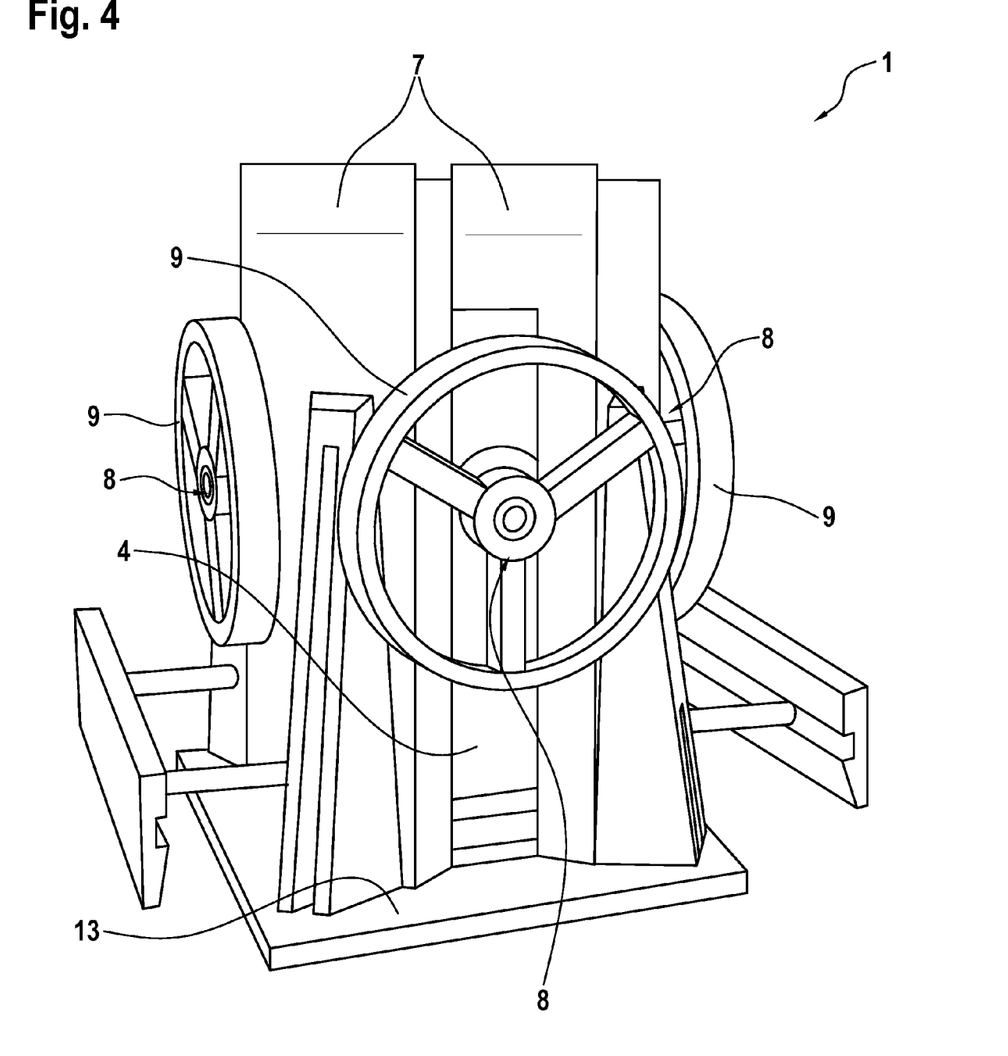
FIG. 4 a second schematic view of the load test stand according to the exemplary embodiment of the invention.

FIG. 4 shows an example of the configuration of the inventive test stand 1, according to the exemplary embodiment. This test stand comprises a frame 13, to which a plurality of independent modules 7 are attached. In this case the modules 7 are in conformity with the configuration of the modules shown in FIGS. 2 and 3. Each of the modules 7 is connected to the flange 5 (which cannot be seen in FIG. 4), so that the flange 5 is mounted on the module 7 in such a way that the modules 7 can perform a tolerance equalization. For example, the effects of temperature fluctuations can be eliminated by this technique, so that the temperature fluctuations do not appear as a source of error in the load test stand 1. Attached to the flange 5 are a plurality of measuring systems 8, which can determine the forces and/or the torques applied by the servo system 4 to the flange 5. In order to improve the measurement procedure and to generate a more realistic simulation, inertial bodies 9 can be mounted on the measuring systems 8. These inertial bodies are designed preferably to simulate rudder inertias or wing inertias. Thus, the influence of these masses of inertia, to which the servo system 4 will be exposed during normal operation, can be simulated with the inventive load test stand 1 of the exemplary embodiment. In order to be able to replace the inertial bodies 9 easily and quickly the inertial bodies are mounted in a floating manner on the measuring system 8.

Figure 5:
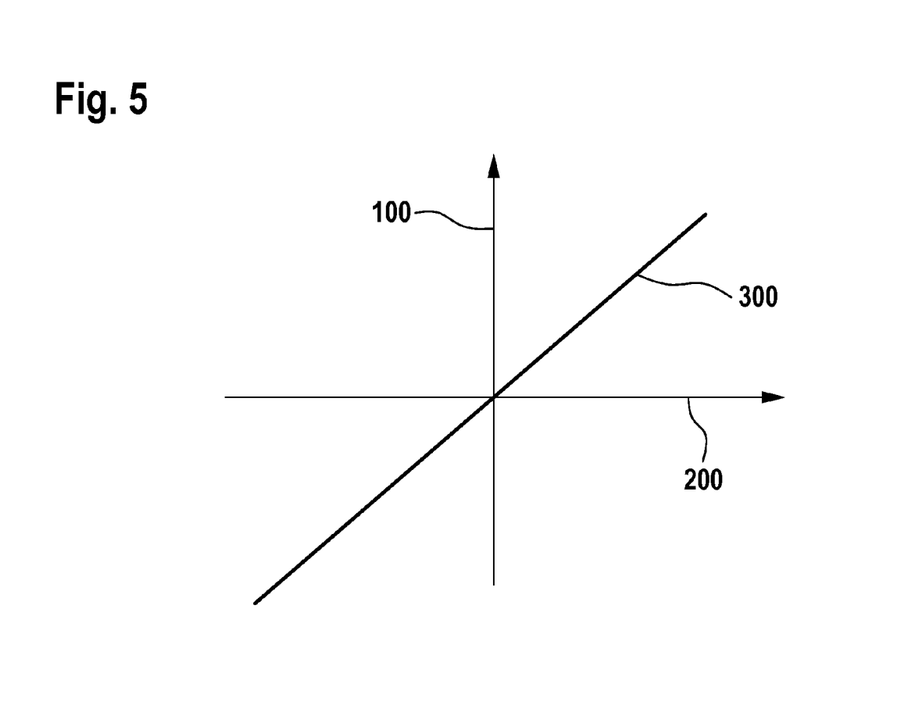
FIG. 5 a graph showing the spring characteristic of a torsion bar.
Figure 6:
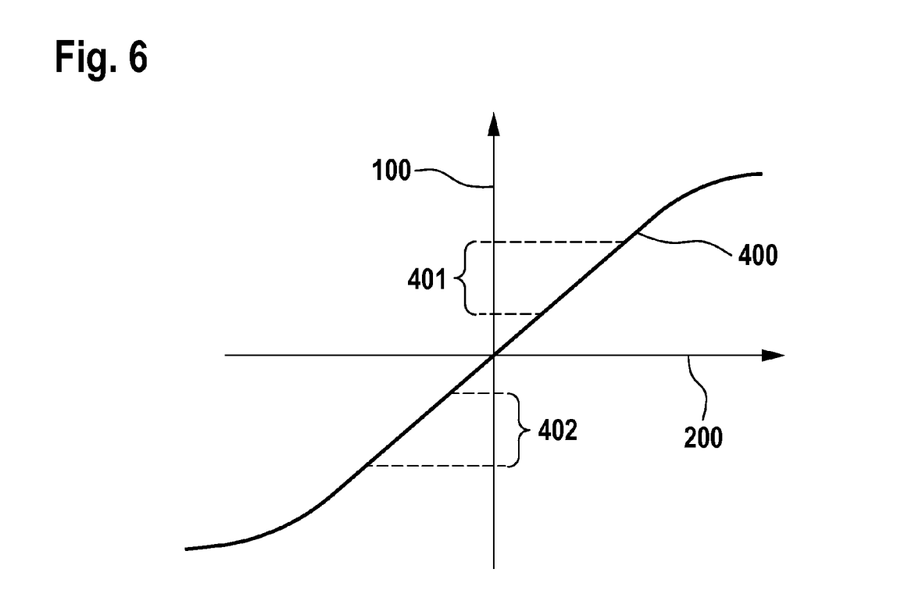
FIG. 6 a graph showing the spring characteristic of the test stand according to the exemplary embodiment of the invention, and FIG. 7 a graph showing an alternative spring characteristic of the load test stand according to the exemplary embodiment of the invention.
Figure 7:
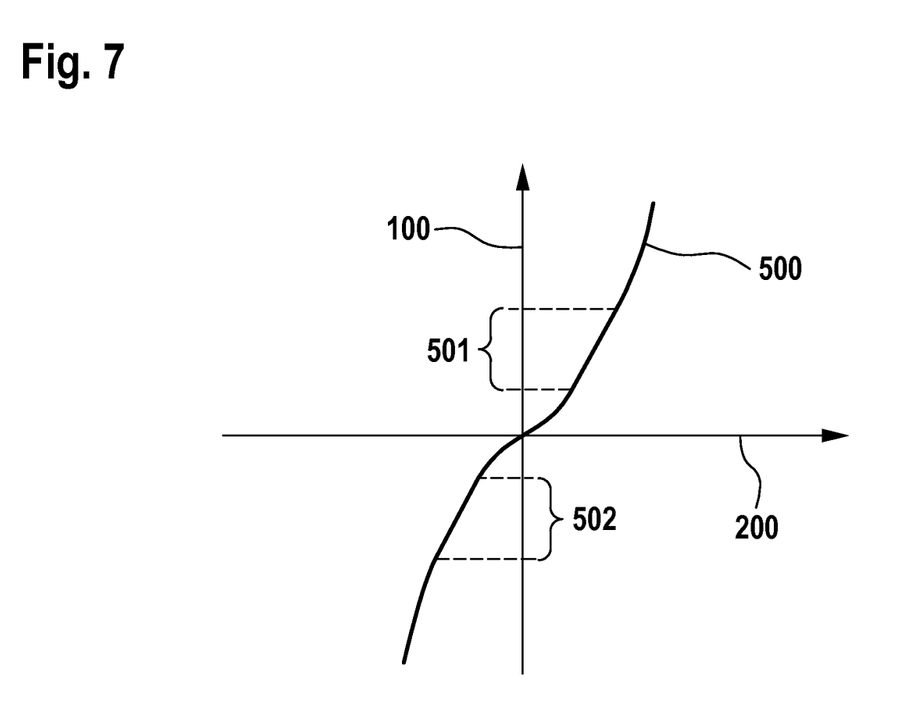

FIGS. 5, 6 and 7 show three different spring characteristics. FIG. 5 shows a first spring characteristic 300 of a torsion bar, whereas FIGS. 6 and 7 show a second spring characteristic 400 of a spring element and a third spring characteristic 500 of a spring element. This situation is illustrated by means of graphs, which always show an instantaneous axis 100 and a torsional axis 200. It is clear from FIG. 5 that the first spring characteristic 300 runs almost linear, which is the major advantage of a torsion bar, a feature that justifies its frequent use in the state of the art. However, FIGS. 6 and 7 show that even the second spring characteristic 400 as well as the third spring characteristic 500 always exhibit linear and/or linearizable ranges.

Hence, a first linear range 401 and a second linear range 402 can be found within the second spring characteristic 400 in FIG. 6. Similarly it is possible to delineate a first linear range 501 as well as a second linear range 502 of the third spring characteristic 500. The inventive use of the above-described load test stand 1 makes it possible to adjust very precisely the spring characteristic of the individual spring elements 3 by changing the frame points 11 and the articulation points 12. Therefore, it is possible to adjust the spring characteristics of the spring elements 3 in such a way that they fall within the linear ranges 401, 402, 501, 502. Such an arrangement makes a measurement with the load test stand, according to the invention, very easy to perform, because an applied torque is almost in proportion to the measured torsion.

Therefore, the inventive load test stand 1, according to the exemplary embodiment shown in the figures, has the following advantageous possibilities:

the ability to adapt the torsion spring characteristic by selecting the kinematic dimensions by means of the articulation positions 12, so that even a plurality of linear sections 401, 402; 501, 502 of the spring characteristic curve 400, 500, which can be adapted to satisfy the test specifications and at the same time jointly cover the respective servo angle ranges, may be rendered possible by means of generatable reverse movements of individual spring excursions within the angular setting range. The net result is a scaling down of the reclamping effort at the output shafts 6 of the servo system 4, so that there is no need to repeat the temperature cycles.

precise positionability of the flange 5 vertically and horizontally and with respect to its neutral angle position.

calibration of the desired spring characteristic for each output shaft 6, for which purpose the respective, in particular separately calibrated, measuring systems 8 are used advantageously for recording the servo angle curves on the output side.

avoidance of an introduction of undefined axial forces into the output shaft 6 of the servo system 4, for example, by means of temperature variations, owing to the axial elastic suspension of the flange 5 in the spring mechanism 2.

protective casing of the spring mechanism 2, which can be integrated into the bearing structure of the whole load test stand 1 and at the same time can exhibit advantageous properties with respect to a reliable actuation of the couplings for connecting the flange 5 to the output shafts 6 of the servo system 4, including an integration possibility of end stops. Such an arrangement makes possible a compact design in view of an accommodation in comparatively small climate chambers, which, in addition, can realize the necessary structural and mechanical properties with respect to the suitability for multi-axis vibration tests.

integration of existing intrinsic inertia in the inertial bodies 9 to be applied on the output side.

applicability of lateral forces with the spring mechanism 2 by changing the position of the frame points (11) after fixing the flange 5 on the output shaft 6 of the servo system 4.

The flat design of the modules 7 allows their arrangement close to the servo system 4, so that a plurality of modules 7 can be connected in parallel, for example, to cover larger torque ranges, overlapping of different characteristic curves of the spring or for separate introduction of lateral forces in any direction.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

LIST OF REFERENCE NUMERALS

1 load test stand
2 spring mechanism
3 spring element
4 servo system
5 flange
6 output shaft
7 module
8 measuring system
9 inertial body
10 torsion bar
11 frame point
12 articulation point
13 frame
14 substructure
20 first axis
30 second axis
40 third axis
100 instantaneous axis
200 torsional axis
300 first characteristic curve of the spring
400 second characteristic curve of the spring
401 first linear range of the second characteristic curve of the spring
402 second linear range of the second characteristic curve of the spring
500 third characteristic curve of the spring
501 first linear range of the third characteristic curve of the spring
502 second linear range of the third characteristic curve of the spring

What is claimed is:

1. A load test stand, comprising
   a frame;
   a flange; and
   a spring mechanism mounted on the frame, wherein the spring mechanism comprises
      a symmetrical arrangement of at least four spring elements,
      frame points connecting the spring mechanism and the frame, and
      articulation points connecting the spring mechanism and the flange,
   wherein the flange is coupleable, by an adapter, to an output shaft of a servo system to be tested.

2. The load test stand, as claimed in claim 1, wherein
   the frame points are mounted in at least one substructure,
   the at least one substructure and the spring mechanism form an adjustable or calibratable independent module,
   the independent module is disposed, by means of a universal interface, on the frame.

3. The load test stand, as claimed in claim 2, wherein the load test stand is configured so that a prestress of the spring mechanism or a position of the flange along a first axis is adjustable by an equidirectional change in a position of at least two frame points of the same at least one substructure.

4. The load test stand, as claimed in claim 1, wherein the load test stand is configured so that a position of the flange along a second axis is adjustable by a change in an opposite direction of a position of at least two opposite frame points.

5. The load test stand, as claimed in claim 1, wherein the load test stand is configured so that a position of the flange along a third axis is adjustable an equidirectional change in a position of at least two opposite frame points.

6. The load test stand, as in claim 1, wherein the load test stand is configured so that a position of the frame points or the bearing points is adjustable by at least one actuator.

7. The load test stand, as claimed in claim 1, wherein the load test stand is configured so that a lateral force on an output shaft connected to the flange is adjustable by changing a position of at least one frame point.

8. The load test stand, as claimed in claim 1, wherein the load test stand is configured so that a spring characteristic of the at least four spring elements is adjustable by a change in a position of the articulation points in such a way that the spring characteristic has linear ranges.

9. The load test stand, as claimed in claim 1, further comprising:
   an angle measuring system arranged at the flange.

10. The load test stand, as claimed in claim 9, wherein the load test stand is configured so that at least one inertial body is coupleable to the measuring system and mountable in a floating manner.

* * * * *